United States Patent [19]

Goldner et al.

[11]  4,431,673
[45]  Feb. 14, 1984

[54] COSMETIC COMPOSITIONS

[75] Inventors: Tibor Goldner, Fresh Meadows, N.Y.; Eustace Fotiu, Mahwah, N.J.; Marlene Tietjen, New York; Kalyan K. Basak, New Hyde Park, both of N.Y.

[73] Assignee: Revlon, Inc., New York, N.Y.

[21] Appl. No.: 306,054

[22] Filed: Sep. 28, 1981

Related U.S. Application Data

[63] Continuation of Ser. No. 146,733, May 2, 1980, abandoned.

[51] Int. Cl.$^3$ .................... A61K 7/021; A61K 7/031; A61K 7/032; A61K 47/00
[52] U.S. Cl. .................... 424/365; 424/DIG. 5; 424/63; 424/357
[58] Field of Search .................. 424/365, 357, DIG. 5

[56] References Cited

U.S. PATENT DOCUMENTS

| | | | |
|---|---|---|---|
| 3,574,822 | 4/1971 | Shepherd | 424/61 |
| 3,860,700 | 1/1975 | Viout et al. | 424/61 |
| 4,000,317 | 12/1976 | Menda et al. | 424/69 |
| 4,107,374 | 1/1978 | Minton | 424/357 |
| 4,116,866 | 9/1978 | Finlayson | 424/357 |
| 4,119,712 | 10/1978 | Goldner et al. | 424/69 |
| 4,126,679 | 11/1978 | Davy et al. | 424/357 |
| 4,151,272 | 4/1979 | Geary et al. | 424/357 |
| 4,177,259 | 12/1979 | Barker et al. | 424/63 |

FOREIGN PATENT DOCUMENTS

| | | | |
|---|---|---|---|
| 2852988 | 6/1979 | Fed. Rep. of Germany | 424/DIG. 5 |
| 2910473 | 9/1979 | Fed. Rep. of Germany | 424/70 |
| 1448041 | 6/1966 | France | 424/63 |

*Primary Examiner*—Dale R. Ore

[57] ABSTRACT

A creaseproof cosmetic composition base containing as essential ingredients in parts by weight:

| | |
|---|---|
| lipophilic emollient | 20–30 |
| volatile solvent | 10–40 |
| hydrophobic fumed silica | 0.2–2 |
| quaternium hectorite | 1–4 |
| waxes | 4–12 |
| wetting agent | 0.5–10 |

5 Claims, No Drawings

COSMETIC COMPOSITIONS

This application is a continuation of application Ser. No. 146,733, filed May 2, 1980, now abandoned.

The present invention relates to cosmetic compositions to be applied in a cosmetic pencil. It particularly relates to creaseproof formulations thus applied.

The cosmetic pencil preparations now in use are either too hard and difficult to apply to an area which is sensitive (i.e., the eyelid), or they are soft and have poor wearing qualities, so that shortly after application they begin to wear off, migrate into crevices in the eyelid and change color. Furthermore, the softer preparations are not suitable for use in cosmetic pencils requiring sharpening since they cannot be readily sharpened with the commonly available pencil sharpeners.

It is, accordingly, an object of the present invention to provide a creaseproof formulation which can be applied in pencil form inside a suitable casing, said formulation being sufficiently hard to be sharpened but not having a degree of hardness that will irritate or otherwise harm the skin on application of the cosmetic thereto.

It is another object of the present invention to provide a creaseproof formulation which is sufficiently firm so that it will not crease, run or liquify but will yield to normal user pressure when applied.

It is a further object of the present invention to provide a creaseproof formulation for use in a pencil applicator, which is readily spreadable, is waterproof and has good wear without showing the usual creasing.

It is still another object of the present invention to provide a creaseproof eye shadow preparation having these desirable properties.

In accordance with the present invention, there is provided cosmetic composition in the form of a firm thixotropic gel comprising a lipophilic emollient, a solvent volatile at room temperature, hydrophobic fumed silica, an organically modified clay, and a wax. Preferably, a wetting agent is also added. This composition can be readily applied in the form of a pencil that can be easily sharpened. The composition spreads readily under pressure and does not run or crease after application. Suitable cosmetic compositions include eye shadows, blushers, spot cover-ups, and the like.

Any lipophilic substance having emollient properties may be used. These include substances such as lanolin and its derivatives, hydrocarbons, phospholipids, fatty acid alcohols, and fatty acid esters. Preferred are esters of long chain alcohols and long chain aliphatic esters. Any ester of a long chain alcohol (one containing from about 10 to 25 carbon atoms) and a long chain aliphatic acid (one containing from about 15 to 25 carbon atoms) is suitable. A preferred ester is the diester, 2-octyldodecyl 12-stearoyloxy-stearate manufactured by Van Dyk & Company, Inc. of Belleville, N.J.

As volatile solvents we prefer to use a volatile silicone such as, for example, cyclomethicone. A preferred solvent is siloxane F-251 which contains a mixture of dimethyl siloxanes comprising, in percent weight, about 20 of siloxanes having 5 silicon atoms, 0 to 5 of siloxanes having 6 silicon atoms, and about 0 to 5 of inert non-volatile substances. The product is available from SWS Silicone Corporation of Adrian, Mich.

Instead of siloxane F-251, other grades of cyclomethicone can be used. The solvent need not be restricted to silicone. Hydrocarbons solvents are also suitable. If the composition is dispensed in the form of a pencil having a plastic casing, it is a necessary condition that the solvent be inert with respect to the plastic.

The hydrophobic fumed silica is an inorganic powdered silica of low bulk density. It is derived from a 99.8% pure fumed silica in which the hydrophilic hydroxyl groups are replaced by trimethylsiloxyl groups. This replacement imparts a number of unique characteristics to the powder, including dry lubricant capabilities, an extremely high degree of water repellency and good skin adhesion. The submicron particle size and large organic surface area enable it to impart its own properties to those of other systems even when present in concentrations as low as 0.1% to 2.0% by weight. This product is commercially available under the tradename Tullanox 500 from Tulco, Inc., North Billerica, Mass.

Suitable organically modified clays are quaternium hectorites. These substances are available as bentones such as bentones 27 and 34, stearalkonium chloride hectorites, arid bentone 38, dimethyl dialkyl (hydrogenated tallow) ammonium chloride hectorite.

Any cosmetically suitable wax or a combination of two or more of such waxes can be used. Suitable waxes are beeswax, ozokerite, candelilla wax, carnauba wax and the like.

A suitable wetting agent, which aids in wetting the pigments and also serves to stabilize the gel structure is a lanolin alcohol or fatty acid. Any lanolin fatty acid is suitable. Other wetting (surface active) agents which may be used include phospholipids, such as lecithin and phytosterols and derivatives thereof, such as alkyl ethers and long chain fatty acid esters.

The preferred creaseproof base compositions of the present invention contain as essential ingredients in parts by weight:

| | |
|---|---|
| emollient | 20-30 |
| cyclomethicone | 10-40 |
| hydrophobic fumed silica | 0.2-2 |
| quaternium hectorite | 1-4 |
| waxes | 4-12 |
| wetting agent | 0.5-10 |

As desired, pigments, dyes, minerals and agents to control the viscosity of the system may be added to obtain the desired color, viscosity and reflectance effects. A suitable agent for controlling the viscosity is propylene carbonate. Other suitable polar agents are ethanol and isopropanol.

Suitable creaseproof compositions according to the present invention are given to Examples I to IV.

EXAMPLE I

| CREASEPROOF SPOT COVER | |
|---|---|
| Propylene glycol dicaprylate/dicaprate | 35.0 |
| Ozokerite | 15.0 |
| Beeswax | 2.0 |
| Hydroxylated Lecithin | .5 |
| Quaternium Hectorite | 2.0 |
| Ethanol | .6 |
| Iron oxides | 3.5 |
| Titanium Dioxide | 10.0 |
| Talc | 10.9 |
| Tullanox 500 | .5 |
| Siloxane F250 | 20.0 |

EXAMPLE II

| CREASEPROOF MAKE UP | |
|---|---|
| Capric/caprylic Triglyceride | 20.0 |
| Myristyl Lactate | 10.0 |
| Candelilla Wax | 6.0 |
| Ozokerite | 6.0 |
| Quaternium Hectorite | 4.0 |
| Propylene Carbonate | 1.2 |
| Iron Oxides | 3.5 |
| TiO2 | 7.5 |
| Talc | 16.5 |
| Tullanox 500 | .3 |
| Siloxane F251 | 25.0 |

EXAMPLE III

| CREASEPROOF BLUSHER | |
|---|---|
| Capric/caprylic triglyceride | 30.0 |
| Candelilla wax | 5.0 |
| Ozokerite | 10.0 |
| Tullanox 500 | .2 |
| Hydroxylated Lanolin | .5 |
| Stearalkonium Hectorite (Bentone 27) | 3.0 |
| Propylene Carbonate | 1.2 |
| Iron oxides | 1.0 |
| Titanium Dioxide | 2.0 |
| Mica | 24.1 |
| Ultramarine Blue | .5 |
| D & C Red 30 Lake on Talc | 2.5 |
| Bismuthoxychloride | 5.0 |
| Siloxane F222 | 15.0 |

EXAMPLE IV

| CREASEPROOF EYE SHADOW | |
|---|---|
| 2-Octyldodecyl 12-stearoyloxy stearate | 20-30 |
| Candelilla Wax | 1-3 |
| Beeswax | 1-3 |
| Carnauba Wax | 1-3 |
| Ozokerite | 1-3 |
| Tullanox 500 | 0.2-2 |
| Lanolin Fatty Acid | 0.5-10 |
| Propylene Carbonate | 0.3-1.2 |
| Quaternium Hectorite | 1-4 |
| Iron Oxide | 5-30 |
| Titanium dioxide | 0-10 |
| Mica | 1-3 |
| Bismuth oxychloride | 0-25 |
| Mica | 5-20 |
| Siloxane F-251 | 15-25 |

Other oxides, e.g., chromium oxide, can be added to vary the color effect.

The compositions of the present invention were readily prepared by charging in a conventional high speed mill such as a Kady mill, the emollient and then adding under high speed milling the quarternium hectorite. Propylene carbonate, where used, and Tullenox 500 were added with continued milling. The colorants (i.e., iron oxide and titanium dioxide) were added and the milling continued until a uniform dispersion was obtained. The temperature of the mixture was then raised to about 85° C. and with continued milling the lanolin fatty acid and waxes added, followed by pearlizing pigments (i.e.g, mica—if desired) and the siloxane F-251. Preferably, the mill was then closed to avoid losses by evaporation, and the milling continued at a low speed until the batch was homogeneous.

The batch, held at a temperature of about 75° to 85° C., was charged into suitable lined containers, for storage.

To prepare the eye shadow pencils, the cosmetic material was remelted to about 75° C. with blending to retain homogeneity and then forced under pressure of about 5 to 15 psi into premolded casings. The casings after filling were provided with end and protector caps.

We claim:

1. A creaseproof, thixotropic cosmetic composition in a firm, solid pencil form containing in parts by weight:

| | |
|---|---|
| lipohilic emollient | 20-30 |
| volatile solvent | 10-40 |
| hydrophobic fumed silica | 0.2-2 |
| quaternium hectorite | 1-4 |
| waxes | 4-12 |
| wetting agent | 0.5-10 |
| pigments | 3-60. |

2. A composition according to claim 1 wherein the volatile solvent is cyclomethicone.

3. A composition according to claim 2 wherein the emollient is a long chain alkyl ester of a long chain aliphatic alcohol.

4. A composition according to claim 3 wherein the long chain alkyl ester of a long chain aliphatic acid is 2-octyldodecyl 12-stearoyloxystearate.

5. A composition according to claim 4 wherein the cyclomethicone is a mixture of dimethyl siloxanes comprising, in percent weight, about 20 of siloxanes having 5 silicon atoms, 0 to 5 of siloxanes having 6 silicon atoms, and 0 to 5 of inert non-volatile substances.

* * * * *